United States Patent [19]
Tom

[11] Patent Number: 5,138,869
[45] Date of Patent: Aug. 18, 1992

[54] IN-LINE DETECTOR SYSTEM FOR REAL-TIME DETERMINATION OF IMPURITY CONCENTRATION IN A FLOWING GAS STREAM

[75] Inventor: Glenn M. Tom, New Milford, Conn.

[73] Assignee: Novapure Corporation, Danbury, Conn.

[21] Appl. No.: 628,490

[22] Filed: Dec. 14, 1990

[51] Int. Cl.$^5$ .............................................. G01N 29/02
[52] U.S. Cl. .................................................. 73/31.03
[58] Field of Search .................... 73/31.03, 23.2, 23.21

[56] References Cited

U.S. PATENT DOCUMENTS 4,960,568 10/1990 Matsumoto et al. ............ 73/23.2 X
5,027,642 7/1991 Wen et al. ...................... 73/31.03 X

OTHER PUBLICATIONS

"System 1/02 Micorprocessor-Based Moisture and Oxygen Content Analyzer", Panametrics, Ltd. (Shannon, Ireland), Mar. 1990.
M Series/Aluminum Oxide Moisture Sensor for Gases and Liquids, Panametrics, Ltd. Shannon, Ireland, Feb., 1990.
System 3A Hygrometer, Panametrics, Ltd., Shannon, Ireland, Dec., 1988.

Primary Examiner—Hezron E. Williams
Assistant Examiner—Joseph W. Roskos
Attorney, Agent, or Firm—Steven J. Hultquist

[57] ABSTRACT

An in-line detector system for real-time detection of impurity concentration in a flowing gas stream in which purified and unpurified volumes of gas from the flowing gas stream are subjected to concentration sensing, to determine a corrected impurity concentration value for the flowing gas stream. The system in a preferred embodiment employs a manifold in flow communication with a purifier unit, a main flow conduit through which the flowing gas stream is passed, and a sensor port, with a selectively positionable valve to flow gas through a purifier loop of the manifold to the sensing port, and alternately through a bypass loop of the manifold without passage through the purifier unit, for comparative impurity sensing of gas in the respective loops. The system may utilize hygrometric sensors in the case of water as a critical impurity, or surface acoustical wave (SAW) devices coated with suitable impurity-affinity coatings. The system has particular utility in monitoring low impurity concentration levels (e.g., from about 0.1 ppm to about 100 ppm) in gas streams employed in vapor-phase processes such as chemical vapor deposition in the manufacture of semiconductor devices.

24 Claims, 2 Drawing Sheets

IN-LINE DETECTOR SYSTEM FOR REAL-TIME DETERMINATION OF IMPURITY CONCENTRATION IN A FLOWING GAS STREAM

BACKGROUND OF THE INVENTION

1. Field of the Invention

This invention relates to means and method for detecting impurity concentration in a flowing gas stream.

2. Description of the Related Art

The rapid expansion of vapor-phase processing techniques, e.g., chemical vapor deposition, in the semiconductor industry has been associated with the deployment and use of manufacturing equipment which is totally reliant on the delivery of ultra-high purity process gases at the point of use in the semiconductor manufacturing facility. Currently, over 5 billion dollars worth of such equipment is in use.

Despite the widespread commercial employment of such vapor-phase processing equipment, little effort has been focused to date on the development of systems for monitoring purity of gas streams in the process system.

As a result of the absence of commercially suitable gas impurity monitoring systems, there is a recurrence of circumstances where a large number of wafers have been processed in the vapor-phase deposition reactor before it is recognized that compositional changes in the process gas stream flowed to the reactor are leading to high rates of rejection. Such high rates of rejection in turn significantly lower the efficiency and productivity of the semiconductor manufacturing plant, and generate substantial losses of potential product. The resulting off-spec microcircuitry articles thus constitute scrap which must be reworked, if this is even feasible, or else discarded as waste.

Accordingly, there is a pressing need in the semiconductor manufacturing industry to provide commercially viable systems for continuously measuring gas purity at the point of use. Such purity measurements can be used to alter process conditions that would otherwise lead to production problems, e.g., by diverting the impurity-containing gas stream to suitable treatment prior to its ultimate use in the deposition process.

In the context of general industrial processes, such as petroleum refining, wastewater treatment, biopharmaceutical production, etc., a variety of impurity monitoring and detection systems have been developed to detect fluid phase impurities, using sampling of a side stream, or slip stream, of the main flow stream for impurity concentration determination. The sampled side stream typically is flowed through the monitoring and detection apparatus and then discarded. In the field of semiconductor manufacture, such wastage is highly detrimental to the economics of the semiconductor production process when the gas stream, as is generally the case, contains costly reagent materials, e.g., organometallic source reagents for metal deposition on a substrate. Further, many gas streams employed in semiconductor manufacturing are highly hazardous in character, so that their waste presents significant difficulties in handling, treatment, and disposal.

Considering the impurities which are present in gas streams involved in semiconductor manufacturing, it is to be noted that the growth of high quality thin film electronic and opto-electronic cells by chemical vapor deposition or other vapor-based techniques is inhibited by a variety of low-level process impurities. These impurities affect both product semiconductor defects and yield.

Specifically, at least two types of contamination are significant, viz., particulate contamination and chemical contamination. Particulate contamination has been successfully addressed by a variety of filtration and collection methods and apparatus (see Malczewski, M. L., et al, "Measurement of Particulates in Filtered Process Gas Streams," Solid State Technology, 28, 151-157, April 1986). Chemical contamination has not received similar attention. As mentioned, the monitoring devices which have been developed in other industries are ill-suited for application to semiconductor manufacturing operations.

In the semiconductor manufacturing operation, chemical impurities in reactive process gases can originate in the production of the source gas itself, as well as in its subsequent packaging, shipment, storage, and handling. Although source gas manufacturers typically provide analyses of source gas materials delivered to the semiconductor manufacturing facility, the purity of such gases may change. Such change may be due to leakage into or outgassing of the containers, e.g., gas cylinders, employed to package such gases. Alternatively, impurity contamination may result from improper gas container changes, leaks into downstream processing equipment, or outgassing of such downstream equipment.

Accordingly, the only comprehensive solution for consistent delivery of high purity gases for vapor processing operations in semiconductor manufacture is the development of commercially useful impurity detection systems for real-time measurement of critical impurity concentrations in semiconductor manufacturing process streams and the deployment of reliable point-of-use purification systems for purifying gas streams which are determined to contain impurity species in excess of allowable concentrations.

The presence of even small concentrations of impurity species in the process gas streams employed in semiconductor manufacturing is potentially deleterious. Even small levels of impurities on the order of parts-per-million (ppm) can cause inconsistent electrical properties in semiconductor devices manufactured by deposition techniques using impurity-containing gas streams.

It therefore is an object of the present invention to provide a system for detection of impurity concentrations in a flowing gas stream, which can be usefully employed in semiconductor manufacturing operations.

It is another object of the present invention to provide a detection system of such type, which is capable of providing real-time monitoring of process gas streams, so that immediate correction can be undertaken when impurity concentration levels exceed predetermined set point limits.

It is a further object of the invention to provide a system for detecting impurity species in flowing gas streams, which is employed in semiconductor manufacturing operations, and which does not require any side stream or slip stream sampling for its utilization.

It is a still further object of the invention to provide a system for detecting impurity concentrations in a flowing gas stream, which is readily calibrated and has a substantial continuous service life, e.g., on the order of at least six months.

Other objects and advantages of the present invention will be more fully apparent from the ensuing disclosure and appended claims.

SUMMARY OF THE INVENTION

The present invention relates to an in-line detector system, useful for real-time determination of impurity concentrations in a flowing gas stream.

In one aspect, the present invention relates to an in-line detector system, comprising:

a purifier unit for gas stream impurity removal; and means defining a flow passage assembly having an inlet end and an outlet end, and constructed and arranged:

for flowing at least a portion of gas from the flowing gas stream through the purifier unit to yield impurity-reduced gas;

for flowing impurity-reduced gas to an impurity concentration sensing locus;

for flowing unpurified gas from the flowing gas stream to an impurity concentration sensing locus; and for discharging the impurity-reduced gas and impurified gas from the outlet end.

In another aspect, the present invention relates to an in-line detector system, comprising:

a purifier unit for removing impurity from gas containing same;

a manifold assembly having an inlet joinable in flow communication to the flowing gas stream for passage of the flowing gas stream therethrough, and an outlet for discharging gas flowed through the manifold assembly, with such manifold assembly defining (i) a first flow path coupled to the purifier unit for passing gas from the flow gas stream through the purifier unit to yield impurity-reduced gas, and (ii) a second flow path bypassing the purifier, constructed and arranged such that the manifold assembly derives from the flowing gas stream first flow path and second flow path gas streams, and discharges same through the outlet of the manifold assembly;

means for (a) sensing gas impurity concentration of impurity-reduced gas discharged from the purifier unit into the first flow path of the manifold assembly, as a baseline impurity concentration value, (b) sensing gas impurity concentration in the second flow path gas stream, and (c) determining therefrom a baseline-adjusted impurity concentration value for the flowing gas stream.

The purifier unit in the broad practice of the invention may be of any suitable type, but preferably comprises a vessel containing a bed of a scavenger material which is sorptively selective for the impurity in the flowing gas stream.

The manifold assembly may be variously configured, and in one aspect may comprise a main gas flow conduit to which is joined, in spaced-apart relationship to one another, the purifier unit and a sensor port coupleable with suitable impurity concentration sensing means. In this assembly, a T-shaped conduit member is utilized having a vertically depending leg joined at a lower end thereof to the main gas flow conduit, and at an upper end thereof to laterally extending arms. The outer ends of the laterally extending arms are respectively joined to the purifier and the sensor port, with a switcher valve, e.g., a pneumatic valve or an electrically controlled solenoid, disposed at the intersection of the arms and leg of the T-shaped conduit member, to selectively establish flow from the main gas flow conduit through the purifier unit to the sensor port, or alternatively through the leg and an arm of the T-shaped conduit member to the sensor port.

Alternatively, the manifold assembly may be configured with an inlet gas flow conduit joined to an inlet gas manifold which at its extremities is joined to respective first and second branch flow conduits, and with the branch flow conduits joined at their opposite ends to an outlet gas manifold which in turn communicates with an outlet gas flow conduit attached to the outlet gas manifold. With such manifold assembly, a purifier unit may be disposed in one of the manifolds or branch flow conduits upstream of a first impurity sensor, while a second impurity sensor is disposed either upstream of the purifier unit, or else in an opposite portion of the manifold assembly through which gas is not flowed to the purifier unit. In this manner the respective impurity sensors constitute a reference sensor (downstream from the purifier unit) and a sample sensor (the sensor deployed in the portion of the manifold assembly through which the gas stream is not flowed to the purifier unit), and the sensing of the reference and sample sensors may be employed to determine a baseline-adjusted concentration value for the impurity in the gas stream.

In a preferred aspect, the impurity concentration sensing means, when water is the impurity species, comprises a hygrometric or alternatively a piezoelectric-based concentration sensor. For non-aqueous impurity species, a piezoelectric-based device preferably is employed, such as a surface acoustical wave (SAW) device.

Another aspect of the invention relates to SAW devices comprising specific affinity coatings on the piezoelectric substrate of the device, as specific to particular impurity gas species.

Other aspects of the invention relate to in-line detector systems of the type broadly described above, as associated with sensors and signal generating and processing means for determining a baseline-adjusted concentration value of the impurity in the flowing gas stream.

Other aspects of the invention include appertaining methodology for determining impurity concentration in a flowing gas stream by in-line detection, wherein gas from the flowing gas stream is purified and sensed to determine its impurity concentration, together with sensing of the impurity concentration of gas from the flowing gas stream which has not been purified, and a calibrated, or baseline-adjusted, concentration value is determined for the impurity in the flowing gas stream.

Other aspects of the invention relate to calibration of sensors, including calibration by using impurity standards which transmit impurity to an impurity concentration sensor through an impurity-permeable membrane.

Other aspects and features of the invention will be more fully apparent from the ensuing disclosure and appended claims.

DETAILED DESCRIPTION OF THE INVENTION, AND PREFERRED EMBODIMENTS THEREOF

Figure 1:
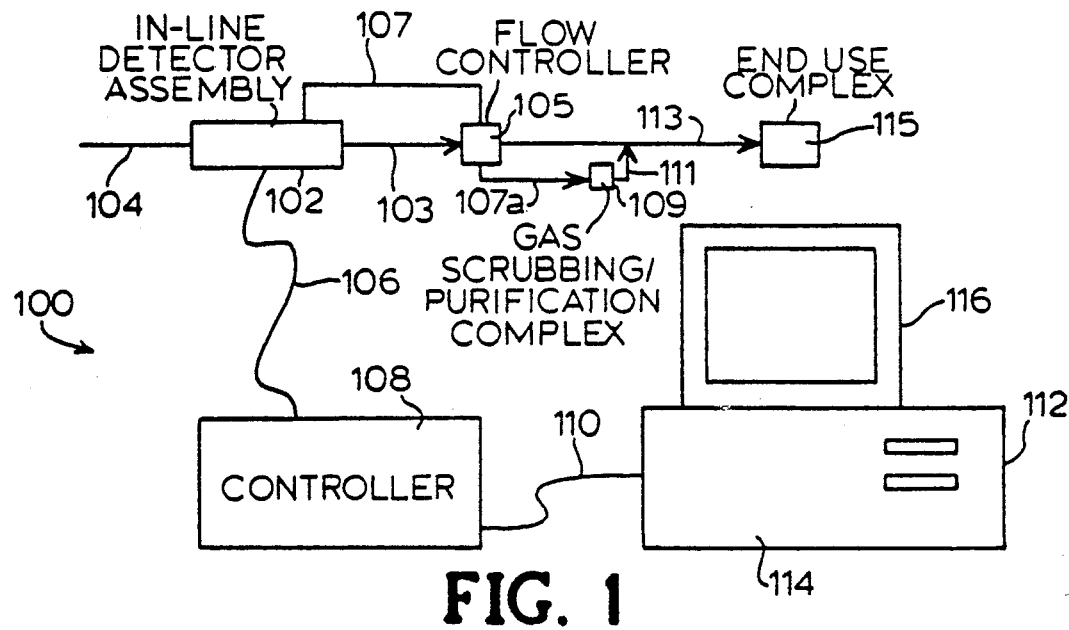
FIG. 1 is a schematic representation of a detector system according to one embodiment of the present invention.

The present invention overcomes the deficiencies of prior art gas monitoring systems, as described in the "Background of the Invention" section hereof, by the provision of an in-line gas impurity detector and monitoring system which is specifically adaptable for use in the manufacture of semiconductor devices including vapor deposition based processes.

The detector system of the present invention enables the concentration of critical impurities in a flowing gas stream to be measured at low levels (e.g., part-per-billion concentrations), thereby permitting impurity concentrations in the flowing gas stream to be maintained at suitably low levels for efficient semiconductor device manufacturing, and may be usefully employed in combination with means for initiating purification treatment of the flowing gas stream when impurities therein exceed acceptable set point limits.

Since the detection system of the present invention is an in-line system, there is no wastage of the process gas, or hazards occasioned by its diversion, treatment, and disposal, such as is the case in impurity concentration monitoring systems in which side streams are separated from the main gas flow stream and passed to remote concentration sensing means.

As a result, the in-line detector systems of the present invention permit consistent delivery of high purity gases to be achieved, with direct, real-time measurement of critical impurity concentrations in process gas streams. In conjunction with the use of such detection systems, the deployment of in-line, point-of-use purification systems enables gas purification to be correctively undertaken so that predetermined purity set point limits for the flowing gas stream are readily and continuously maintained.

Examples of gas purification systems which may be usefully employed in conjunction with the in-line detector systems of the present invention, include the purifier apparatus, compositions, and methods disclosed and claimed in U.S. Pat. No.: 4,761,395 (composition for purification of arsine, phosphine, ammonia, and inert gases); U.S. Pat. No. 4,853,148 (hydrogen halide purification); U.S. Pat. No. 4,797,227 (hydrogen selenide purification); U.S. Pat. No. 4,781,900 (method of purifying arsine, phosphine, ammonia, and inert gases); U.S. Pat. No. 4,950,419 (inert gas purification); U.S. Pat. No. 4,865,822 (hydrogen selenide purification method); and U.S. Pat. No. 4,925,646 (hydrogen halide purification method); as well as the purifier vessel apparatus disclosed and claimed in U.S. Pat. Nos. 4,723,967 and 4,738,693, all of which hereby are incorporated herein by reference.

The in-line detector systems of the present invention may be utilized with any suitable specific gas impurity concentration sensors, which provide output indicative of impurity concentration in the gas stream. Such sensors may be hygrometric (in the case of monitored aqueous contaminants such as water), spectrophotometric (based on transmissivity or reflectivity of radiation impinged on the gas stream), piezoelectric, colorimetric, etc., in character or may otherwise incorporate any suitable means, method, or modality of operation, as desired, for quantitation of the selected impurity species in the flowing gas stream being monitored.

Generally, in semiconductor manufacturing operations, the most critical impurity species is water vapor, and the presence of water in the gas stream often is indicative of atmospheric contamination of the process system. Accordingly, the invention will be illustratively described hereinafter primarily with reference to detection of water as the impurity species of interest. It will be recognized however, that such focus is for descriptive purposes only and that the invention is broadly practicable in monitoring of any other impurity species, for which suitably sensitive sensors exist.

While the specific structure and function of the in-line detector systems may be widely varied within the broad scope of the present invention, such in-line detection systems must meet various functional criteria, as set out below.

First, the detector system must be non-contaminating in character, with respect to the gas stream being processed. Since the flowing gas stream after its monitoring (and verification of suitably low impurity concentration therein) is flowed to the deposition reactor or other locus of use, any contaminants deriving from the detector system will subsequently be distributed throughout the process system. This may have a significant and deleterious effect on the products being manufactured. Accordingly, any impurities introduced from the in-line detector system itself should be suitably low, e.g., in the part-per-billion (VX) range or lower.

Thus, the detector system must be mechanically tight and leak-free in character. This requirement dictates the use of correspondingly suitable materials of construction in the detector system, with the parts and components of the detector system having a high finish on those parts and components which are in contact with the gas stream, and with all seals of the detector being of a face seal, leak-tight character.

A preferred material of construction is stainless steel of suitably high finish quality. If any particulates are generated in the use and operation of the detector, particle filters may be required components of the system.

In addition, the detector system should accurately measure the critical impurities in the process stream. Process gas streams employed in the semiconductor manufacturing industry typically contain more than one impurity, and it would be highly advantageous to accurately measure the concentration of each of such impurities in the gas stream.

As a practical consideration, however, there does not exist a single sensor which is able to measure all possible impurities. Monitoring all impurities of interest would therefore require a large multiplicity of sensor devices, which would in turn unduly complicate the design and operation of the detector system.

Accordingly, in multicomponent impurity-containing gas streams, it is preferable to select a single impurity species and monitor same, particularly where the impurity species monitored is a limiting or most critical impurity, or where the specific impurity species is quantitatively correlative with other impurity species present in the multicomponent impurity-containing gas stream.

As indicated hereinabove, a critical impurity in semiconductor manufacturing operations is water, and a variety of water sensors is readily available. By contrast, oxygen, while also an important impurity species, is frequently a poor choice for process gas monitoring purposes, since oxygen sensors are poisoned by many of the (semiconductor manufacturing) gas streams of interest, so that as a practical matter, viable sensors are not available. In this respect, it should be borne in mind that the sensors required are preferably sub-part-per-million (ppm) level sensors.

Thus, the detector system should have the requisite sensitivity for detection of gas impurities, preferably on the level of parts-per-million and most preferably on the level of parts-per-billion.

Further, the detector system should be stable for substantial periods of time, e.g., at least six months, and preferably on the order of one year or more, without recalibration continually being required. Thus, the sensors used in the detector should be of a non-drifting character, or if drift is necessarily present, means should be provided to self-correct the concentration measurement so that stable and consistent quantitative operation is achieved, with respect to the impurity concentration in the gas stream being monitored.

Additionally, the cost of the detector system should be suitably low to ensure ready commercial deployment, with economic, readily available sensor devices being utilizable in the detector system.

The foregoing criteria are accommodated in the broad practice of the present invention by the provision of a detector system in which gas from the flowing gas stream (either a portion of such stream, or the entire stream itself) is passed through a purifier in which the impurity being monitored is substantially completely removed from the gas. The impurity concentration of the resulting purified gas is then sensed to provide a baseline concentration sensing value. Contemporaneously, gas from the flowing gas stream, which is not purified by the aforementioned purifier unit, is subjected to impurity concentration sensing means. This provides a sensed concentration value which is employed, together with the impurity concentration sensing valve for the purified gas, to provide a calibrated value of impurity concentration for the flowing gas stream.

The gas passed through the purifier and subsequently sensed for impurity concentration, is discharged from the detector system in the flowing gas stream, and the sensed gas which has not been purified likewise is discharged from the detector system in the flowing gas stream. By this arrangement, none of the influent flowing gas stream passed through the detector system is diverted to waste, or otherwise requires final disposition as a result of its being monitored for impurity content (the only exception is the impurity species which is removed from gas in the purifier, e.g., which is typically present in the gas flowed to the purifier at a low concentration, e.g., less than about 1,000 ppm and more typically less than 100 ppm).

Correspondingly, the sensor which is employed with the in-line detector system should have a suitably low detection limit, preferably sub-ppm levels, and more preferably down to 100 parts-per-billion (Vui), or lower.

Among the various types of sensor devices described hereinabove (hygrometric, spectrophotometric, etc.), a preferred sensor is of piezoelectric-type, in which the characteristics of the piezoelectric surface thereof are altered by the presence and any change in concentration of the impurity species being monitored in the detector system.

A particularly preferred piezoelectric device comprises a surface acoustical wave (SAW) device. SAW devices are piezoelectric electronic components which traditionally have been used as narrow band frequency filters, e.g., frequency-determining elements in high frequency control applications. Such devices operate by passing a signal across a piezoelectric thin planar substrate as an acoustic wave. The acoustic wave is created by imposing an AC electrical signal on a metallized interdigital electrode which is plated on the surface of the substrate at one end. This acoustic wave is transmitted across the substrate to a symmetrically formed metallized interdigital electrode (transducer) at the opposite end. The receiving transducer converts the acoustic signal back to an electric signal. The electrical characteristics of SAW devices can be tailored to specific application by varying the finger spacing of the interdigital transducers, the space between transducers, and the thickness of the substrate, as is well known to those skilled in the art, to control the frequency, propagation delay, and acoustic wave mode of the signal transmitted across the device.

Regardless of the specific type of impurity concentration sensor employed in the broad practice of the present invention, the sensor should possess the sensitivity to measure the concentration of the critical impurities at sufficiently low levels consistent with the high purity character of the gas streams being monitored by the detection system.

Referring now to the drawings, FIG. 1 shows a schematic diagram of an in-line detection system 100, comprising an in-line detector assembly 102. Conduit 104 is joined to the detector assembly and conveys the high purity gas stream to the assembly for monitoring therein of the concentration of critical impurity species. Monitored gas is discharged from the detector assembly in line 103 and is passed to flow controller 105, which is coupled to the detector assembly in signal transmitting relationship by means of flow control signal line 107a. If the monitoring of the critical impurity species reveals that the concentration is above set point limits, the flowing gas stream is diverted by the flow controller 105 into bypass line 107 and flows into gas scrubbing or purification complex 109 in which the impurity species is removed to below the maximum set point concentration value. The resulting scrubbed gas then is passed in line 111 to the process gas delivery conduit 113 and is discharged into the vapor-phase processing complex 115.

If the concentration of the critical impurity species monitored by detector assembly 102 is within allowable set point limits, the flowing gas stream in line 103 is passed by the controller 105 to delivery line 113 for passage to the downstream, end use complex 115. Complex 115 may, for example, comprise a chemical vapor deposition reactor or other suitable downstream processing equipment.

Joined to the in-line detector assembly 102 in signal transmitting and receiving relationship, via signal line 106, is a controller 108. This controller may include optoelectronic converters, digital/analog circuitry, etc., by means of which the sensing of impurity species by the in-line detector assembly 102 is convertible to a processing signal. This processing signal is transmitted by signal transmitting means 110 to a digital computer 112 comprising central processing unit 114 and monitor or display 116. Alternatively, the digital computer 112 may be replaced by microprocessor means which are incorporated in or otherwise integrated with the controller 108.

In operation of the FIG. 1 system, the in-line detector assembly 102, coupled with a suitable sensor or sensors, is arranged to sense concentration of critical impurity species in the flowing gas stream, as well as to sense the critical impurity species concentration of gas from the flowing gas stream which has been subjected to purification.

These respective concentration sensings then are passed by signal transmitting means 106 to controller 108, and converted to the requisite form (of a processing signal) for computational purposes. The processing signal is passed by processing signal transmitting means 110 to digital computer 112 for determination of an on-line, real-time concentration value, as corrected (normalized) by the purified gas (impurity concentration sensing) value.

The normalization (correction) of sensing of critical impurity species in the flowing gas stream, by correspondingly sensing the critical impurity species in a purified stream of the gas from the bulk flowing gas stream passed to the in-line detector, is a critical aspect of the present invention, which eliminates problems that may occur in sustained operation of the detector system as a result of sensor "drift".

Thus, with the high sensitivities desired of the sensors in the broad practice of the present invention, e.g., below 1000 parts-per-million, preferably below 100 parts-per-million, more preferably below 10 parts-per-million, and most preferably below one part-per-million, the sensors invariably have a tendency to drift (change in accuracy) with time. This is particularly true in continuous operation or near-continuous operation semiconductor manufacturing plants, in which gas is flowed through the detector system over sustained periods of time. Such alteration of sensitivity and accuracy of the sensors with time, unless continuously corrected, can insidiously lead to gas impurity concentrations exceeding proper set point limits without being identified as "out of spec". This in turn may cause excessive amounts of impurities to be present in layers and films deposited on substrates in the subsequent vapor-phase processing operations. The resulting inclusions of gross amounts of impurity species in product devices which can render them deficient or even useless for their intended purpose The drift problems associated with high sensitivity sensor(s) in the detection system are self-corrected in the practice of the present invention, by sensing the concentration of impurity species in gas derived from the bulk flow stream, after it has been purified in an in-line fashion, with such purified gas impurity sensing then being employed as a baseline corrective value or condition for the sensing of impurities in the (unpurified) bulk flow stream.

By "in-line detection" as used herein is meant that the flowing gas stream of interest is sensed as to its impurity concentration, and also is at least in part purified to provide a baseline impurity concentration sensing, with both sensings being carried out in the same general locus, and with any gas in circulation loops employed for sensing purposes being redirected into the bulk gas flow stream for ultimate delivery to the downstream processing facility, e.g., chemical vapor deposition reactor.

Figure 2:
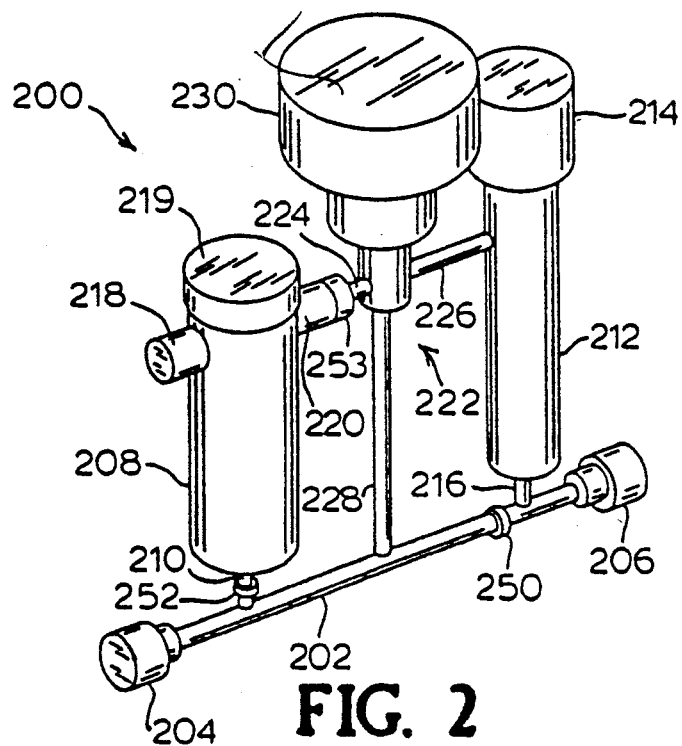
FIG. 2 is a perspective view of a detector system assembly according to one aspect of the present invention.

Referring now to FIG. 2, there is shown a perspective view of an in-line detector assembly 200, comprising a main gas flow conduit 202 with an inlet fitting 204 at one end, and a discharge fitting 206 at the opposite end thereof. The main gas flow conduit 202, by means of the respective inlet and discharge fittings 204 and 206, may be coupled in an "in-line" fashion to a gas stream which ultimately is passed to a chemical vapor deposition (CVD) reactor, or other vapor-phase processing apparatus.

A purifier vessel 208 is joined in inflow relationship to the main conduit 202 by means of purifier feed conduit 210.

As appearing subsequently herein, identifications of a component of the detector system being joined "in inflow relationship" to another component of the system, means that the components are constructed and arranged so that the gas stream flows from the first-mentioned component to the second-mentioned component. Correspondingly, the identification of a detector system component as being joined "in outflow relationship" to another system component, means that the respective components are constructed and arranged so that the gas stream from the first-mentioned component is discharged (through any suitable flow communication means) to the second-mentioned component of the system.

Downstream of the purifier feed conduit 210, and in proximity to the discharge fitting 206, is provided an impurity sensor port 212, with an upper fitting 214. By means of the upper fitting 214, the sensor port may be coupled to a suitable sensor, such as a hygrometric sensor for water vapor detection, or a SAW device for detection of water, nitrogen oxides, hydrogen sulfide, or other critical impurity of interest. The sensor port 212 is joined to the main flow conduit 202 by means of sensor port feed conduit 216.

The purifier unit 208, depending on the impurity species, may comprise a fluid-tight vessel filled with a bed of a suitable scavenger material. The scavenger material may for example comprise a scavenger of a type as disclosed in U.S. Pat. Nos. 4,761,395; 4,853,148; 4,797,227, in a purifier vessel of the type disclosed and claimed in U.S. Pat. No. 4,723,967 or U.S. Pat. No. 4,738,693. The purifier vessel 208 may suitably be provided, if desired, with a pressure transducer port 218, for measurement of pressure in the purifier unit. The purifier vessel 208 also features an outlet port 220, by means of which purified gas is discharged from the purifier unit.

The detector assembly shown in FIG. 2 further comprises a manifold 222 interconnecting the purifier unit 208 with the sensor port 212, by means of lateral conduits 224 and 226. The manifold also is joined to the main flow conduit 202 by means of vertical conduit 228.

By this construction, the manifold 222 is T-shaped, with lateral conduits 224 and 226 forming the respective arms at the top of the T, and with the vertical conduit 228 forming the leg of the T. Disposed in the manifold 222, at the locus of intersection of the conduits 224, 226, and 228, is a switcher valve 230. This valve preferably is an automatic control-type valve which is selectively switchable between (1) a first position for effecting flow of gas through the manifold, in conduits 224 and 226 thereof, from the purifier unit 208 to the sensor port 212, and (2) a second position for effecting flow of gas to the manifold from the main flow conduit 202, and through vertical conduit 228 and lateral conduit 226 to the sensor port 212.

Disposed in the main flow conduit 202 upstream of sensor port feed conduit 216 is a first flow restrictor 250. A second flow restrictor 252 is disposed in purifier unit feed conduit 210. A third flow restrictor 253 is disposed in manifold 222, at the outlet of discharge port 220 of purifier unit 208, and the junction of the purifier unit outlet port with lateral conduit 224.

The first, second, and third flow restrictors may be of any suitable type which are adaptable to provide the flow restriction and pressure drop characteristics necessary in the detector system. The flow restriction characteristics of these three flow restrictions may include different pressure drops, as in the illustrative detector system herein described. Alternatively, in some instances it may be desirable for the flow restriction characteristics of all of the flow restrictors to be the same. The flow restrictors preferably comprise disk-shaped elements, or "frits," constructed of sintered metal, porous ceramic, or other flow-permeable medium which is compatible with the gas stream constituents, and is efficacious for its intended purpose in terms of pressure drop and flow restriction character. In addition to their pressure drop and gas flow regulating functions, flow restrictors 252 and 253 assist in retaining the scavenger material in purifier unit 208.

Preferred restrictor elements include stainless steel frits which are commercially available from Mott Corporation (Farmington, Conn.). Such elements are available in the form of 40 micron average pore size disks, which may suitably be employed for the first flow restrictor 250 and second flow restrictor 252, and in the form of 5–100 micron average pore size disks, which may be usefully employed for flow restrictor 253.

In operation of the system shown in FIG. 2, the inlet fitting 204 of the main gas flow conduit 202 may be coupled to piping or tubing through which the bulk gas stream is flowed to the detector system, and the discharge fitting 206 of such conduit is likewise coupled to suitable piping or tubing for the delivery of the bulk gas flow stream to the downstream processing apparatus. The major portion of the bulk gas stream flows through the main conduit 202, with the first flow restrictor 250 creating a small amount of back pressure. This back pressure forces a small amount of gas from the main flow stream into either the purifier unit feed conduit 210 or the vertical conduit 228 of manifold 222, depending on the setting of the switcher valve 230 The switcher valve suitably is coupled to automatic controller means (not shown), such as a microprocessor-controlled timer actuator for the valve. The switcher valve may be of any suitable type; preferred types include pneumatic valves and electrically controlled solenoids.

Flow restrictor 252 and flow restrictor 253 provide containment of the scavenger or other sorbent material which is provided in the form of a bed in purifier unit 208. As a result of gas flow through the bed of scavenger or sorbent material in the purifier unit, particulates may otherwise be susceptible of migrating into feed conduit 210 or manifold conduit 224, if the restrictors 252 and 253 were not present. In addition, flow restrictors 252 and 253 provide back pressure for the purifier loop defined by feed conduit 210, purifier unit 208, discharge port 220 and conduits 224 and 226 of manifold 222.

When the switcher valve 230 is selectively positioned in a first position, gas from the main gas flow stream in conduit 202 flows through purifier unit feed conduit 210 into purifier unit 208 where the impurity species is removed from the gas to produce an impurity-reduced gas stream. This purified gas stream is discharged from the purifier unit in discharge port 220, and passes through flow restrictor 223 and conduits 224 and 226 to the sensor port 212 for sensing by a sensor (not shown) which is operatively joined to the sensor port by means of coupling 214.

If the switcher valve 230 is switched to a second position, the gas flowing in conduit 202 will bypass the purifier loop and gas will flow through conduits 228 and 226 of the manifold 222, and enter the sensor port 212, so that sensing of the impurity concentration in the gas stream can be effected. Regardless of whether the gas entering the sensor port 212 passes through the purifier loop, or passes through manifold conduits 228 and 226, the gas is discharged therefrom in sensor conduit 216 to the downstream portion of main conduit 202, for discharge through the outlet fitting 206 into the connecting piping or tubing (not shown) and delivery to the downstream processing apparatus.

By this arrangement, utilizing the respective flow restrictors, all of the gas flows in the detector assembly can be manipulated by a single valve. The sensor port 212 may be coupled with a suitable sensor, e.g., an alumina hygrometer sensor, by means of sensor coupling 214.

By means of the detector assembly in FIG. 2, the monitoring of gas impurity concentration is carried out with no waste stream. All flows from the main flow conduit passing to the sensor port are returned to the main gas flow stream with no loss. Further, the detector assembly comprises a purifier unit which provides a non-drifting zero measurement point. As a result, it is possible to continuously correct the sensor in the course of operation of the detector assembly, yielding a stable sensing system for extended periods of time. In addition, since the impurity-containing gas from the main gas flow stream, as well as the impurity-reduced gas yielded by the purifier unit, are passed sequentially to a common sensor port, the utilization of a single sensor is facilitated, which obviates the problems associated with differing drifts of accuracy and sensitivity when multiple sensors are employed.

While the present invention preferably is practiced by using a single sensor in connection with the in-line detection assembly of the invention, as for example is accommodated by the detector assembly shown in FIG. 2, the invention may also be carried out with multiple sensors, as will be described more fully hereinafter. It is to be recognized that the use of multiple sensors, due to the aforementioned drift phenomena, may require periodic recalibration in order to maintain accurate and reliable monitoring of gas impurities in gas streams flowed through the detector assembly.

Figure 3:
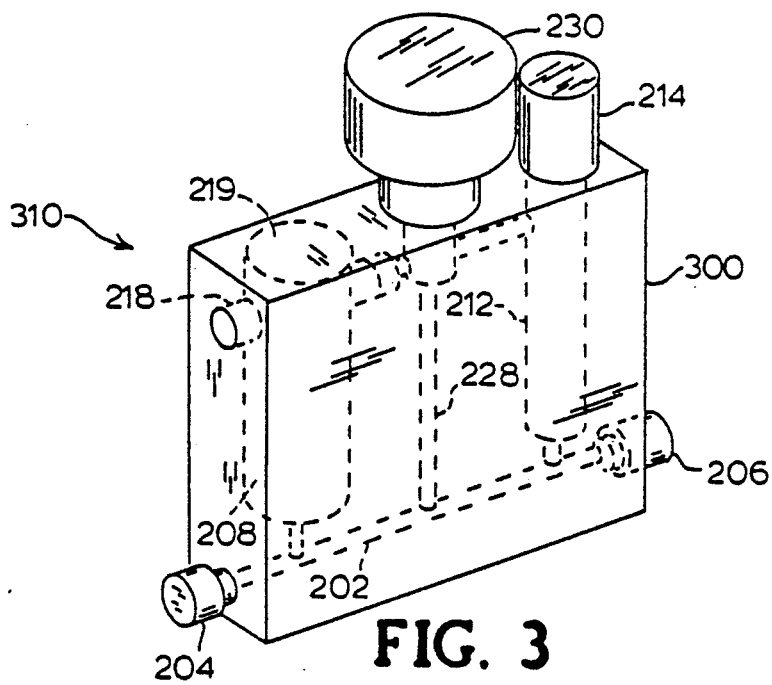
FIG. 3 is a perspective view of the detector system assembly of FIG. 2, schematically shown as being mounted in a modular housing.

Referring now to FIG. 3, the detector assembly of FIG. 2 is shown as being encased in a unitary housing 300, which may be of block-like form as shown, with the inlet port 204, outlet port 206, purifier pressure transducer port 218, purifier unit fill port 219, switcher value 230, and sensor port coupling 214 extending exteriorly of the housing 300. By this arrangement, the overall detector assembly 310 represents a unitary, easily mounted structure, which is readily deployed, in-line, in a bulk gas flow stream for detection of impurity concentrations therein.

As a specific illustrative embodiment of a detector assembly of the type shown in FIGS. 2 and 3, with respect to the flow restrictors 250, 251, and 252 employed therein, flow restrictor 250 may comprise a 0.2 inch diameter stainless steel element having an average pore size of 40 microns, and a surface area of 0.2 cm$^2$, providing an estimated pressure drop, at one liter per minute (1 pm) of gas flow, of 0.15 pounds per square inch (psi).

Flow restrictor 252 may comprise another 40 micron average pore size stainless steel element of large diameter. Due to its large diameter, it presents no significant pressure drop. For example, a DB1000 Mott Corporation p6 flow restrictor will have a 0.09 psi pressure drop, for a superficial flow rate of 2830 1 pm/ft$^2$ (0.03 psi/1 pm/cm$^2$).

Flow restrictor 253 may suitably comprise a 0.2 inch diameter 10 micron average pore size stainless steel element. The estimated pressure drop for this restrictor element is about 5 times greater than the pressure drop for the corresponding 40 micron average pore size element. Accordingly, the flow which is directed through the purifier loop (conduit 210, purifier unit 208 and manifold conduits 224 and 226) will be approximately 20% of the main flow stream entering the detector assembly in main conduit inlet 204, when the switcher valve 230 is deployed to effect flow through the purifier loop.

Figure 4:
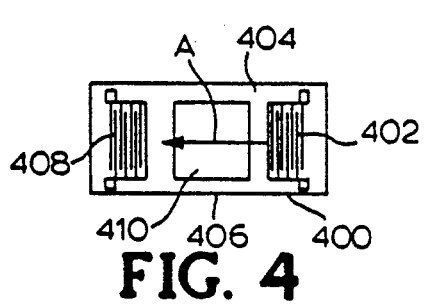
FIG. 4 is a top plan view of a surface acoustical wave detector, such as may be usefully employed in the practice of the invention to sense impurity concentrations in flowing gas streams.

FIG. 4 is a top plan view of a SAW device, comprising a metallized interdigital electrode 402 provided on the surface 404 of a substrate formed by a piezoelectric thin planar base. At the opposite end of the SAW device from the first metallized interdigital electrode 402 is a corresponding metallized interdigital electrode 408. Intermediate the respective interdigital electrodes 402 and 408 is a surface coating 410 formed of a material having affinity for the particular impurity species of the gas stream to be monitored using the SAW device.

The interdigital electrode 402 in the structure shown constitutes a transmitter, and the interdigital electrode 408 constitutes a receiver, with the transmitter being appropriately electrically energized to generate an acoustic wave which is transmitted across the substrate surface 404 over the surface coating 410, and subsequently received by the receiver electrode 408. The direction of propagation of the acoustic wave is shown in FIG. 4 by arrow A.

Thus, in operation, the acoustic wave is generated from an AC electrical signal delivered to electrode 402 (by means not shown) following which the wave traverses the impurity affinity coating 410 and is received by the opposite electrode 408, for reconversion to an electrical signal. The reconverted electrical signal then is transmitted, e.g., by signal transmitting means 106 shown in detector system 100 in FIG. 1, to a controller, from which a computational signal is sent to a digital computer, microprocessor, or other calculational means, to quantitatively determine the impurity concentration of the gas with which the impurity-affinity surface of the SAW device is contacted.

Figure 5:
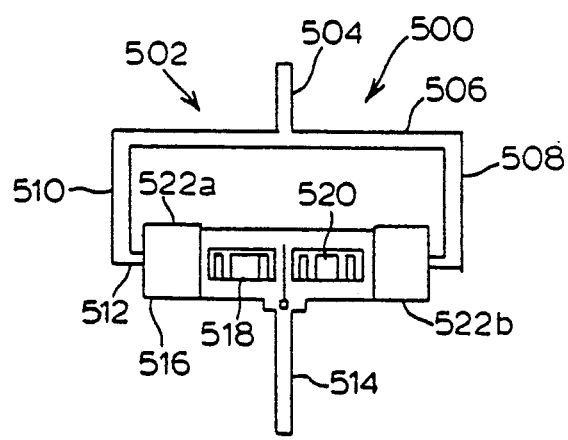
FIG. 5 is a schematic representation of a detector system according to another embodiment of the invention, utilizing surface acoustical wave devices in respective branches of a manifold assembly, for establishing a calibrated (baselineadjusted) value of impurity concentration in a flowing gas stream.

FIG. 5 is a schematic representation of a detector system 500 according to another embodiment of the present invention.

As illustrated, the detector assembly 500 comprises a manifold 502 including an inlet conduit 504 joined to inlet manifold conduit 506. The manifold conduit 506 is joined at one end to branch conduit 508, and at its opposite end to branch conduit 510, as shown. Each of these respective branch conduits is also joined to outlet manifold conduit 512, having disposed in each of its respective legs, on either side of discharge conduit 514, a SAW device. The left-hand leg of discharge manifold conduit 512, as illustrated in FIG. 5, has a purifier unit 516 upstream of SAW device 518. In the right-hand leg of the outlet manifold conduit 512 is disposed a coupling fitting 522, upstream of SAW device 520. The discharge conduit 514 is joined to discharge manifold conduit 512, such that gas streams flowed across the respective SAW devices 518 and 520 are recombined at the intersection of the left-hand and right-hand legs of such discharge manifold conduit, and then discharged from the manifold 502 in discharge conduit 514.

In the FIG. 5 detector assembly, the passage of the gas through the left-hand leg of the discharge manifold conduit 512 entails passage of the gas through purifier 516 to deplete impurity species from the gas stream, following which the gas stream is sensed as to its residual impurity concentration, by SAW device 518. Concurrently, the gas stream in the right-hand leg of discharge manifold conduit 512 is passed through coupling 522 and across SAW device 520, for sensing of the impurity species concentration in the (unpurified) gas stream.

In this manner, the influent gas stream in inlet conduit 504 is split into two respective streams, one of which is passed through a purifier to remove impurity species therefrom. Both gas streams then are sensed as to their impurity concentrations, with the sensings being employed to generate signals which are algorithmically utilized to determine a corrected (baseline-adjusted) value of impurity species concentration in the gas stream flowed through the detector assembly 500.

The SAW devices employed in the detector system shown in FIG. 5 may suitably be of the type discussed in connection with FIG. 4. SAW devices are usefully employed as chemical sensors in the broad practice of the present invention, due to their ability to respond to changes caused by the binding of atoms and molecules to the SAW device surfaces which lie in the path of the transmitted acoustic wave. The response of the SAW device can take either the form of a surface wave amplitude attenuation, or, more commonly, the form of a change in the wave velocity. These changes, in turn, result from the formation of a thick surface layer of bound material (in the case of SAW devices used in the present invention, a layer of the impurity species bound to the affinity substrate), which differs from the SAW substrate lacking such bound impurity species, in terms of elasticity, mass density, viscosity, and/or conductivity.

SAW devices can be applied as gas sensors, as well as for sensing of liquid deposited on the SAW affinity surface. For gas sensing operations, a Rayleigh mode acoustic wave normally is employed; for liquid phase sensing, various acoustic wave modalities may be employed, including the Rayleigh mode, horizontal shear plate mode, or flat plate mode acoustic waves. In the broad practice of the present invention, for gas impurity sensing, Rayleigh mode SAW gas sensors are preferably employed.

Mathematically, the effect of depositing a layer of foreign material on the top surface of a SAW device (e.g., surface 404 of device 400 in FIG. 4), can be predicted by either formulating a complete set of equations which describe wave propagation in the layer, wave propagation in the SAW device substrate, and boundary conditions, or by modeling the SAW device system through pertubation theory, as described, for example, in Auld, B.A., "Acoustic Fields and Waves in Solids," Wiley-Innerscience, New York, Vol. 2, Ch. 12. If the deposited layer of foreign material is so thin as to be less than an acoustic wavelength, then pertubation theory may advantageously be employed, with the velocity change due to the deposition of a thin isotropic layer being described by the equation:

$$\frac{\Delta V}{V} = -\left[\frac{h\rho'V\omega}{2\mu}\right] \times \left\{[U_x^2 + U_y^2 + U_z^2] - \left[4\left(\frac{\mu'}{\rho'V^2}\right)U_x^2 + \frac{4\mu'(\lambda' + \mu')}{\rho'V^2(\lambda + 2\mu')}U_x^2\right]\right\}$$

wherein V is surface wave velocity, p is density, $\mu$ and $\lambda$ are elasticity constants, and h is the thickness of the thin film and V', $\rho'$, $\mu'$ and $\lambda'$ refer to the deposited thin film properties. The above equation is referenced to a surface wave propagating in the x direction along a substrate having thickness in the z dimension. The quantity $|U_i|2/4P$ is a normalized particle displacement component which is a function of the acoustic wave mode propagating in the substrate and the physical properties of the SAW substrate. Such displacement components have been calculated for many materials, and it is known that they are greatest in the x and z dimensions for Rayleigh mode waves. Thus, Rayleigh mode waves yield the highest mass response sensitivity and are the operating mode of choice for gas sensing applications where wave attenuation is not a problem.

An examination of the above equation reveals that the change in velocity is proportional to mass per unit area, $h\rho'$, and this relationship provides the theoretical basis of mass response for SAW devices. It should also be noted that velocity change is a function of frequency of operation. As a consequence, the sensitivity of mass response of a SAW device increases with frequency. Inasmuch as SAW devices are capable of operating at frequencies higher than one GigaHertz (GHz), extremely high mass sensitivities can be achieved, on the order of 1-10 picograms/cm$^2$.

The foregoing equation also predicts that differences in the elasticity of the thin film material deposited on the SAW device surface will have a second order effect on velocity change (described by the final term of the equation). Since the SAW device will respond to any mass that adsorbs or attaches to the surface across which the wave is transmitted, the sensing surface of the SAW must be modified to render the surface selective only for the specific desired impurity of interest in the broad practice of the present invention. Thus, the primary consideration in developing a SAW device for sensing a specific analyte is providing on the sensing surface of the SAW device a surface coating which will selectively bind the analyte of interest, while not binding, or only weakly binding, other components found in the gas stream.

In the detector system illustratively shown and described with reference to FIG. 5, the same coating (film 410 on the SAW device as shown in FIG. 4) is employed on both sensors 518 and 520, with the purifier 516 removing the critical impurity species from the process gas stream diverted into branch conduit 510 from inlet manifold conduit 506. In this manner, the gas impurity sensing which is effected by SAW device 518 serves as a reference sensing. By measuring the difference in velocity changes in the respective SAW devices 518 and 520, the effect of the strongly bound analyte is isolated, without interference from other gas stream components or changes in such variables as temperature or pressure.

The high sensitivity of SAW devices in gas impurity sensing applications is well known and established in the art, and various reports have been published demonstrating the utility of SAW devices in specific impurity-containing gas systems. For example, Vetelino, J. F., et al, IEEE Trans. Ultrason., Ferroelec. Freq. Control, UFFC-34(2), 156–161 (1987) describes the use of a SAW device having a surface coating of $WO_3$ as employed for sensing of hydrogen sulfide, with sensitivity to concentrations of hydrogen sulfide of less than 10 ppm. Venema, A., et al, IEEE Trans. Ultrason., Ferroelec. Freq. Control, UFFC-34(2), 148–155 (1987) reports the use of a coating of copper phthalocyanine, an organic semiconductor, on a SAW device to sense nitrogen dioxide ($NO_2$) with a threshold detection sensitivity of 500 Vui. Both of these reported applications involve the use of dual SAW device configurations to compensate for nonspecific effects.

In the operation of detector systems according to the present invention, initial calibration is required, even when multiple sensors are employed.

Figure 6:
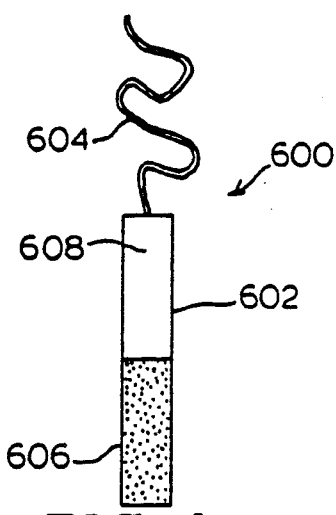
FIG. 6 is a schematic representation of a permeation tube device which may be used as a calibration standard for gas impurity sensors employed in the practice of the present invention.

FIG. 6 is a schematic representation of a calibration device which may be usefully employed in the practice of the present invention to provide initial calibration for a known impurity concentration. As shown in FIG. 6, the calibration device 600 comprises a container 602 having disposed therein an impurity constituent liquid 606. Above this impurity liquid is a vapor space 608 in vapor flow communication with a permeation tube 604, which is formed of a permeable membrane material which allows the out-diffusion of the impurity species into the gas surrounding the permeation tube. The permeation tube may be formed of a suitable polymeric material having known and controllable permeability characteristics, e.g., polytetrafluoro-ethylene, or other suitable polymeric or, alternatively, non-polymeric material.

Consistent with the criticality of water as an impurity species in semiconductor manufacturing operations, the calibration device 600 shown in FIG. 6 may suitably contain as the liquid 606 a quantity of water. With the homogenous structure of the permeation tube 604, the diffusion of permeant (water) at constant temperature will also be constant. The water vapor diffusing out of the permeation tube, through the surface along its length, then may be passed into a carrier gas, e.g., a previously purified gas stream (with respect to impurity therein), to provide a constant, known concentration of impurity for calibration of the SAW device or other sensor element in the practice of the present invention. The calibration device 600 shown in FIG. 6 affords a simple, and highly reducible, means for supplying known impurity levels at sub-ppm concentrations.

The permeation tube 604 of the calibration device may itself be calibrated either gravimetrically or by measuring the water level of the liquid 606 in container 602, using a commercially available trace moisture analyzer, such as for example a DuPont 5700 Moisture Analyzer, available from E. I. DuPont de Nemours and Company (Wilmington, Del.), which is capable of detecting moisture levels as low as 10 Vui.

With reference to the specific impurity species-binding coating (see surface 410 on SAW device 400 in FIG. 4), an acceptable coating must meet the following criteria:

(1) the coating must reversibly bind the impurity species in a suitable concentration range of interest (e.g., water in a 10-100 Vui range);

(2) the coating must bind the impurity in the presence of the reactive gases of interest, with a minimum of interference from the process gas stream;

(3) the coating must be non-contaminating with respect to the gas streams of interest;

(4) the coating must be stable over an extended period of time; and (5) the coating must be easily and reproducibly applied to the sensing surface of the SAW device.

Even when considering a single impurity species such as water, it is apparent that no universal hygroscopic coating exists for all possible gas streams of interest which may contain such (water) impurity. In the case of water as an impurity, it is expected that inert gases and hydride gases of Group IV-VI elements of the Periodic Table will be able to use the same moisture-affinity coating. The impurity-affinity coating employed for sensing of water impurity in hydrogen halide gases, however, will be different.

In the case of inert and hydride reactive gases (including those of Group IV-VI elements), a poly(vinylamine) coating may potentially usefully be employed in the broad practice of the present invention, provided that such coating meets the criteria (1)-(5) stated above. Amines are know to reversibly bind water, and, in fact, an amine coating is employed in the aforementioned DuPont 5700 Moisture Analyzer which, as noted, has a sensitivity in the 10 Vui range, and has been employed successfully in inert gas as well as arsine moisture-sensing service.

The molecular weight of the poly(vinylamine) is desirably high enough so that the polymer will have no appreciable vapor pressure which would otherwise contaminate the gas stream being monitored for impurity concentration. The poly(vinylamine) polymer is non-degradable in hydride gas streams, so that such polymer is non-contaminating in the gas streams being monitored.

In addition, poly(vinylamine)s are soluble in polar solvents, so that they are readily applied to SAW device surfaces, e.g., by spin-coating of polar solvent solutions of such polymers. Suitable poly(vinylamine)s are commercially available from Polysciences, Inc. (Warrington, Pa.) and may be usefully employed in as-purchased form, for dissolution into polar solvents and application to the sensor surface by suitable application techniques such as spin coating.

When moisture is the critical impurity to be sensed in hydrogen halide gas streams, a suitable coating material for the SAW device affinity surface comprises poly(vinylsulfonic acid). This material is the acid equivalent to the poly(vinylamine) coating discussed above, and is usefully employable for affinity surface coatings on SAW devices in hydride gas service. Poly(vinylsulfonic acid) is commercially available from Polysciences, Inc. and may be employed in as-furnished form by dissolution into a suitable solvent, and application, e.g., by spin coating, to the sensing surface of the SAW device.

The aforementioned illustrative polymeric materials employed to coat the sensor surface of the SAW device may be spun coated by aqueous solutions thereof.

After the SAW device is coated with the impurity-affinity layer or film, the detection capability thereof may be tested using calibrated standards such as the calibration device 600 shown and described with reference to FIG. 6 above. In the course of such calibration testing, the response of the coating is measured, and the coating is modified if necessary to achieve the desired highly sensitive, stable, and reproducible sensor layer required in the detection system of the present invention.

Figure 7:
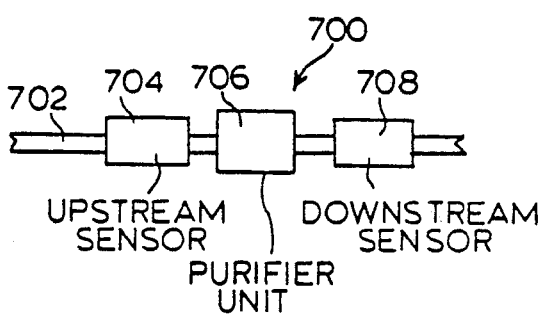
FIG. 7 is a schematic representation of an in-line detector system according to a further embodiment of the present invention.

FIG. 7 is a schematic representation of a detector assembly according to another embodiment of the present invention. As shown, the detector assembly 700 comprises an upstream sensor 704, a purifier unit 706, and a downstream sensor 708 mounted in conduit 702 through which the impurity-containing gas stream is flowed. The upstream sensor 704 and downstream sensor 708 may comprise SAW devices of the type illustratively shown and described with reference to FIG. 4 hereof, and the purifier unit 706 may suitably comprise a purifier along the lines f purifier unit 208 (in the system shown and described with reference to FIG. 2 hereof).

In operation, the impurity-containing gas stream flows through conduit 702 into a housing containing upstream sensor 704, which senses the impurity concentration of the gas flow stream, and discharges the sensed gas flow stream into conduit 702 for passage to purifier unit 706. In purifier unit 706, the critical impurity species is removed by sorption, chemical reaction, or other suitable removal modality, to yield an impurity-depleted or impurity-reduced gas. The purified gas is passed in conduit 702 to downstream sensor 708, which senses the impurity level in the purified gas stream discharged from purifier unit 706. After sensing of the critical impurity species concentration in the purified gas, the purified gas stream is discharged from sensor 708 into conduit 702 and passed to downstream use and/or further treatment operations.

The detector assembly shown schematically in FIG. 7 differs from the detector assemblies shown and described with reference to FIGS. 2, 3, and 5, in that such previously described systems utilize the separation of a part of the main gas flow stream for purification and subsequent sensing purposes, to establish a baseline or corrective sensing for impurity concentration determination. In FIG. 7, the entire bulk gas flow stream is passed through the respective sensors, with a purifier unit interposed therebetween, so that the downstream sensor provides a baseline or corrective sensing of the purified gas. However, the detector system of FIG. 7, as well as the system schematically shown n FIG. 5, comprises the use of two discrete sensors. By contrast, the gas detector assembly shown in FIGS. 2 and 3 permits the use of a single gas sensing element, with both purified and unpurified portions of the flowing gas stream being sequentially passed to the same sensor port for monitoring purposes. Accordingly, sensor "drift" in the detector assembly of FIGS. 2 and 3 is obviated by use of a single sensor device, as previously discussed.

Although the invention has been described with respect to particular features, aspects, and embodiments thereof, it will be apparent that numerous variations, modifications, and other embodiments are possible within the broad scope of the present invention, and accordingly all variations, modifications, and embodiments are to be regarded as being within the spirit and scope of the invention.

What is claim is:

1. An in-line detector system for sensing concentration of an impurity species in a flowing gas stream, said system comprising:
    a purifier unit for gas stream impurity removal; and
    means defining a flow passage assembly having an inlet end and an outlet end, and constructed and arranged:
        for flowing at least a portion of gas from the flowing gas stream through the purifier unit to yield impurity-reduced gas;
        for flowing impurity-reduced gas to an impurity concentration sensing locus;
        for flowing unpurified gas from the flowing gas stream to an impurity concentration sensing locus; and
        for discharging the impurity-reduced gas and unpurified gas from the outlet end;
    wherein the impurity concentration sensing locus for unpurified gas, and the impurity concentration sensing locus for impurity-reduced gas, comprise different loci.

2. An in-line detector system for sensing concentration of an impurity species in a flowing gas stream, said system comprising:
    a purifier unit for gas stream impurity removal;
    means defining a flow passage assembly having an inlet end and an outlet end, and constructed and arranged:
        for flowing at least a portion of gas from the flowing gas stream through the purifier unit to yield impurity-reduced gas;
        for flowing impurity-reduced gas to an impurity concentration sensing locus;
        for flowing unpurified gas from the flowing gas stream to an impurity concentration sensing locus; and
        for discharging the impurity-reduced gas and unpurified gas from the outlet end; and
    an upstream concentration sensor, a downstream concentration sensor, and the purifier unit interposed therebetween, disposed in the means defining the flow passage assembly such that the upstream sensor, purifier unit, and downstream sensor are in series relationship to one another.

3. An in-line detector system for sensing concentration of an impurity species in a flowing gas stream, said system comprising:
    a purifier unit for gas stream impurity removal;
    means defining a flow passage assembly having an inlet end and an outlet end, and constructed and arranged:
        for flowing at least a portion of gas from the flowing gas stream through the purifier unit to yield impurity-reduced gas;
        for flowing impurity-reduced gas to an impurity concentration sensing locus;
        for flowing unpurified gas from the flowing gas stream to an impurity concentration sensing locus; and
        for discharging the impurity-reduced gas and unpurified gas from the outlet end;
    wherein the means defining the flow path assembly comprise:
        (i) an inlet gas manifold having first and second ends;
        (ii) an inlet gas flow conduit joined to the inlet gas manifold intermediate the first and second thereof;
        (iii) an outlet gas manifold having first and second ends;
        (iv) a first branch conduit connecting the respective first ends of the inlet and out gas manifolds;
        (v) a second branch conduit connecting the respective second ends of the first and second gas manifolds; and
        (vi) an outlet gas conduit joined to the outlet gas manifold intermediate the first and second ends thereof;
    further comprising a first impurity concentration sensor disposed in the out gas manifold between the first end thereof and the junction of the outlet gas conduit with the outlet gas manifold;
    the purifier unit being positioned in the outlet gas manifold intermediate the first end thereof and the first gas impurity concentration sensor therein; and
    further comprising a second gas impurity concentration sensor in the gas outlet manifold intermediate the first end thereof and the junction of the outlet gas manifold with the outlet gas conduit.

4. A detector system according to claim 3, further comprising signal transmission means connecting the first and second gas impurity concentration sensors with means for determining the impurity concentration of gas flowing into the inlet gas conduit.

5. A system according to claim 4, wherein the impurity concentration determining means comprise a digital computer.

6. A detector system according to claim 3, wherein the first and second gas impurity concentration sensors comprise a SAW device.

7. An in-line detector system for real-time detection of impurity concentration in a flowing gas stream, comprising:
    a main flow conduit having inlet and outlet ends joinable in closed flow communication to the flowing gas stream for flow of the gas stream therethrough;
    a gas stream impurity sensor port jointed in outflow relationship to an outlet end portion of the main flow conduit;
    a purifier unit for gas stream impurity removal, joined in inflow relationship to an inlet end portion of the main flow conduit;
    a manifold (11 interconnecting the purifier unit in outflow relationship to the impurity sensor port, and (2) joined to the main flow conduit intermediate the junctures of the sensor port and purifier unit therewith;

a switching valve disposed in the manifold and switchable between (i) a first position for effecting flow of gas through the manifold from the purifier unit to the sensor port, and (ii) a second position for effecting flow of gas through the manifold from the main flow conduit to the sensor port; and a first flow restrictor disposed in the main flow conduit upstream of and in proximity to the junction between the main flow conduit and the sensor port.

8. A detector system according to claim 7, further comprising gas impurity concentration sensor means operatively coupled to the gas stream impurity sensor port.

9. A detector system according to claim 8, wherein the gas impurity concentration sensor means comprises a hygrometric sensor.

10. A detector system according to claim 9, wherein the hygrometric sensor comprises an alumina-based hygrometer.

11. A detector system according to claim 8, wherein the gas impurity concentration sensor means comprises a SAW device.

12. A detector system according to claim 11, wherein the SAW device comprises an impurity-affinity coating formed of a material selected from a group consisting of poly(vinylamine) and poly(vinylsulfonic acid).

13. A detector system according to claim 8, wherein the gas impurity concentration sensing means has a lower concentration sensitivity in the range of from about 1 Vui to about 1 ppm.

14. A detector system according to claim 8, further comprising signal transmission means connecting the gas impurity concentration sensor means with means for determining the impurity concentration of gas flowing to the gas stream impurity sensor port.

15. A detector system according to claim 14, wherein the impurity concentration determining means comprise a digital computer.

16. A detector system according to claim 7, further comprising:

a second flow restrictor disposed at the junction between the main flow conduit and the purifier unit; and a third flow restrictor disposed in the manifold between the purifier unit and the sensor port.

17. A detector system according to claim 16, wherein the first and second flow restrictors have substantially similar pressure drop characteristics, and the third flow restrictor has a pressure drop characteristic which is substantially greater than either of the pressure drop characteristics of the first or second flow restrictors.

18. A detector system according to claim 7, further comprising a gas impurity sensor disposed in sensing communication with the sensor port.

19. A detector system according to claim 18, further comprising an input signal generating means, and an output signal processing means, coupled to said gas impurity concentration sensor.

20. A detector system according to claim 7, wherein the main flow conduit, purifier unit, manifold, and flow restrictor, and sensor port are all mounted in a unitary housing, whereby the detector system can be modularly coupled to a flowing gas stream.

21. A method of sensing gas impurity concentration in a flowing gas stream, comprising:

purifying at least a portion of the flowing gas stream to yield impurity-reduced gas;

sensing gas impurity concentration of the impurity-reduced gas;

sensing concentration of unpurified gas from the flowing gas stream; and discharging all gas which has been sensed for impurity concentration in the flowing gas stream, wherein the impurity concentration sensing locus for unpurified gas, and the impurity concentration sensing locus for impurity-reduced gas, comprise different loci.

22. A method according to claim 21, comprising splitting the flowing gas stream into first and second portions, purifying only the first portion, with the second portion comprising said unpurified gas, and after impurity concentration sensing of the first and second portions at said different loci recombining the first and second portion and discharging same as a reconstituted flowing gas stream.

23. A method of sensing gas impurity concentration in a flowing gas stream, comprising:

purifying at least a portion of the flowing gas stream to yield impurity-reduced gas;

sensing gas impurity concentration of the impurity-reduced gas;

sensing concentration of unpurified gas from the flowing gas stream; and discharging all gas which has been sensed for impurity concentration in the flowing gas stream, wherein the flowing gas stream is passed, in series, through an upstream gas concentration sensor, a purifier unit, and a downstream concentration sensor.

24. A method of sensing gas impurity concentration in a flowing gas stream, comprising:

providing an in-line detector system in closed flow communication with the flowing gas stream, said in-line detector system comprising:

a main flow conduit having inlet and outlet ends joinable in closed flow communication to the flowing gas stream for flow of the gas stream therethrough;

a gas stream impurity sensor port joined in outflow relationship to an inlet portion of the main flow conduit;

a purifier unit for gas stream impurity removal, joined in inflow relationship to an inlet end portion of the main flow conduit;

a manifold (1) interconnecting the purifier unit in outflow relationship to the impurity sensor port, and (2) joined to the main flow conduit intermediate the junctures of the sensor port and purifier unit therewith;

a switching valve disposed in the manifold and switchable between (i) a first position for effecting flow of gas through the manifold from the purifier unit to the sensor port, and (ii) a second position for effecting flow of gas through the manifold from the main flow conduit to the sensor port; and a flow restrictor disposed in the main flow conduit upstream of and in proximity to the junction between the main flow conduit and the sensor port;

passing gas from the flowing gas stream into the in-line detector system;

sequentially switching said switching valve to flow gas from the flowing gas stream alternately through the manifold from the purifier unit to the sensor port, and through the manifold from the main flow conduit to the sensor port;

sensing concentration of gas impurity in the gas at said sensor port;

determining from the gas impurity concentration sensing at the sensor port a corrected concentration measurement for impurity concentration in the flowing gas stream; and discharging gas from the sensor port to the flowing gas stream.

* * * * *